United States Patent [19]
Matsumoto et al.

[11] Patent Number: 5,880,283
[45] Date of Patent: *Mar. 9, 1999

[54] 8-ALKOXYQUINOLONECARBOXYLIC ACID HYDRATE WITH EXCELLENT STABILITY AND PROCESS FOR PRODUCING THE SAME

[75] Inventors: Toyomi Matsumoto, Kamiina-gun; Masamoto Hara, Okaya; Kunio Miyashita; Yukihiro Kato, both of Okaya, all of Japan

[73] Assignee: Kyorin Pharmaceutical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 860,325

[22] PCT Filed: Dec. 5, 1995

[86] PCT No.: PCT/JP95/02477

§ 371 Date: Jun. 23, 1997

§ 102(e) Date: Jun. 23, 1997

[87] PCT Pub. No.: WO96/19472

PCT Pub. Date: Jun. 27, 1996

[30] Foreign Application Priority Data

Dec. 21, 1994 [JP] Japan ................................ 6-335569

[51] Int. Cl.⁶ ........................ C07D 401/10; C07D 401/04
[52] U.S. Cl. ............................................................ 544/363
[58] Field of Search ................................................ 544/363

[56] References Cited

U.S. PATENT DOCUMENTS

| | | | |
|---|---|---|---|
| 3,985,747 | 10/1976 | Kaplan et al. | 260/243 |
| 4,442,101 | 4/1984 | Ichihashi et al. | 424/250 |
| 4,544,658 | 10/1985 | Petersen et al. | 544/363 |
| 4,980,470 | 12/1990 | Masuzawa et al. | 544/363 |
| 4,997,943 | 3/1991 | Iwata et al. | 544/363 |
| 5,597,923 | 1/1997 | Nagano et al. | 546/156 |

*Primary Examiner*—Mukund J. Sham
*Assistant Examiner*—Ann Kessinger
*Attorney, Agent, or Firm*—Oblon, Spivak, McClelland, Maier, & Neustadt, P.C.

[57] ABSTRACT

The invention provides 1-cyclopropyl-6-fluoro-1,4-dihydro-8-methoxy-7-(3-methyl-1-piperazinyl)-4-oxo-3-quinolinecarboxylic acid sesquihydrate with excellent stability represented by a following formula (1),

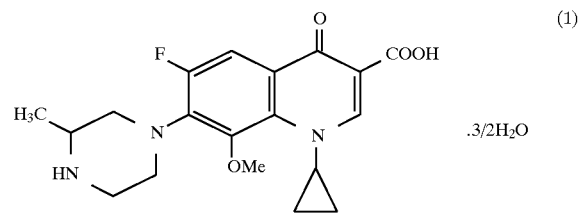

and process for producing the same.

9 Claims, 7 Drawing Sheets

8-ALKOXYQUINOLONECARBOXYLIC ACID HYDRATE WITH EXCELLENT STABILITY AND PROCESS FOR PRODUCING THE SAME

TECHNICAL FIELD

The present invention relates to 1-cyclopropyl-6-fluoro-1,4-dihydro-8-methoxy-7-(3-methyl-1-piperazinyl)-4-oxo-3-quinolinecarboxylic acid sesquihydrate with excellent stability and process for producing the same.

BACKGROUND TECHNOLOGY

Antibacterial agents of the quinolonecarboxylic acid class have achieved a striking progress in recent years. Because of broad antibacterial spectrum and potent bactericidal activity ranging from Gram-positive bacteria to negative bacteria, they have become to be used for surgical infectious diseases as well as urinary tract infectious disease and their usefulness is highly appreciated, leading to great contribution in the clinical practice.

1-Cyclopropyl-6-fluoro-1,4-dihydro-8-methoxy-7-(3-methyl-1-piperazinyl)-4-oxo-3-quinolinecarboxylic acid is particularly noted because of not only its potent antibacterial activity but also higher selectivity against bacteria from mammalian cells, which brings on an excellent selective toxicity.

In Japanese Unexamined Patent Publication No. Sho 62-252772, hemihydrate of 1-cyclopropyl-6-fluoro-1,4-dihydro-8-methoxy-7-(3-methyl-1-piperazinyl)-4-oxo-3-quinolinecarboxylic acid represented by a formula (2) is disclosed.

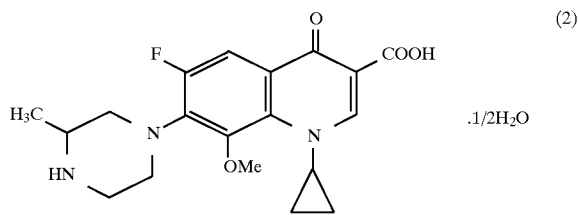

(2)

1-Cyclopropyl-6-fluoro-1,4-dihydro-8-methoxy-7-(3-methyl-1-piperazinyl)-4-oxo-3-quinolinecarboxylic acid tends to make a hydrate because of its strong hygroscopicity, and it easily forms a hemihydrate when recrystallizing from water-containing organic solvent or when drying crystals obtained by the recrystallization method by neutralization according to acid-alkali recrystallization.

It was revealed by us, however, that the measured weight of this hemihydrate increases with the rise of environmental humidity. It was further revealed by us that the tablet containing the hemihydrate has poor disintegration and dissolution rates, leading to disadvantages in pharmaceutical manufacturing.

Moreover, in Japanese Unexamined Patent Publication No. Sho 63-198664, hydrochloride of 1-cyclopropyl-6-fluoro-1,4-dihydro-8-methoxy-7-(3-methyl-1-piperazinyl)-4-oxo-3-quinolinecarboxylic acid represented by a formula (3) is disclosed.

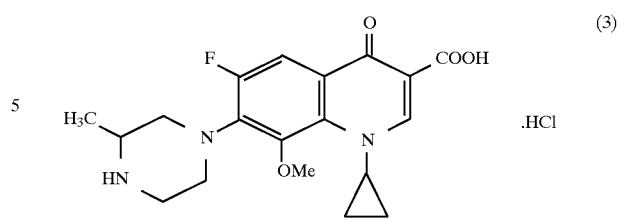

(3)

However, with respect to this hydrochloride (3), too, the instability due to the hygroscopicity of drug substance same as or more than that of hemihydrate (2) and the problems of poor disintegration and dissolution rate when converted to tablets have become evident.

DISCLOSURE OF THE INVENTION

As a result of studies for the purpose of solving the problems of said 1-cyclopropyl-6-fluoro-1,4-dihydro-8-methoxy-7-(3-methyl-1-piperazinyl)-4-oxo-3-quinolinecarboxylic acid hemihydrate and hydrochloride, the inventors have found that 1-cyclopropyl-6-fluoro-1,4-dihydro-8-methoxy-7-(3-methyl-1-piperazinyl)-4-oxo-3-quinolinecarboxylic acid sesquihydrate is a stable compound and excellent also in pharmaceutical manufacturing. Namely, 1-cyclopropyl-6-fluoro-1,4-dihydro-8-methoxy-7-(3-methyl-1-piperazinyl)-4-oxo-3-quinolinecarboxylic acid sesquihydrate has been found to be stable under different conditions of humidity, and the disintegration and dissolution rates of the tablets manufactured have also found to be good.

In addition, as a means to obtain 1-cyclopropyl-6-fluoro-1,4-dihydro-8-methoxy-7-(3-methyl-1-piperazinyl)-4-oxo-3-quinolinecarboxylic acid sesquihydrate, we have found that the target compound can be obtained efficiently by heating an aqueous suspension of 1-cyclopropyl-6-fluoro-1,4-dihydro-8-methoxy-7-(3-methyl-1-piperazinyl)-4-oxo-3-quinolinecarboxylic acid under stirring, leading to the completion of the invention.

Here, the aqueous suspension represents a suspension after neutralization in the acid-alkali recrystallization during the process for purification, a suspension of isolated crystals added with water, or the like, and it is possible to manipulate with amount of water 3 to 20 times as much as crystals, but it is preferable to use 3 to 5 times for obtaining the target compound in high yield.

It is optimum to stir for 10 to 30 minutes at a temperature of, for example, 50° to 100° C., preferably 80° to 90° C.

The pH of aqueous suspension is preferable to be in the vicinity of neutrality (6.0–8.0).

After collecting the first crop of the target compound by filtration, the second crop can be obtained by cooling the filtrate to room temperature, which may result in an increase of overall yield.

BEST EMBODIMENT FOR PUTTING THE INVENTION INTO PRACTICE

In following, the invention will be illustrated in more detail showing an example, but the invention is not subject to any restriction by this example.

(EXAMPLE 1)

1-Cyclopropyl-6-fluoro-1,4-dihydro-8-methoxy-7-(3-methyl-1-piperazinyl)-4-oxo-3-quinolinecarboxylic acid (85 g) was suspended into water (425 ml, 5 times volume) and stirred for 10 minutes at an inner temperature of 80° to 85° C. After hot filtration at the same temperature, the crystals were dried to obtain the target compound (84.43 g) at a yield of 92.7%.

Elemental analysis: $C_{19}H_{22}FN_3O_4 \cdot 3/2H_2O$

|  | C | H | N | Water content |
|---|---|---|---|---|
| Calculated | 56.71 | 6.26 | 10.44 | 6.7 |
| Found | 56.79 | 6.15 | 10.44 | 7.3 |

(1) Instruments Used

TG/DTA: Rigaku Corporation (TAS-200; Control section), TG8101D2 (Measuring apparatus)

Infrared spectrophotometer: Hitachi, Ltd., Model 270-30

Powder X-ray diffraction apparatus: Rigaku Corporation, Model 2013

Single crystal X-ray diffraction apparatus: Rigaku Corporation Model AFC5R

Karl Fischer moisture meter: Kyoto Electronics Manufacturing Co., Ltd., Model MKA-3P 1) Thermal analysis (TG/DTA)

Figure 1:
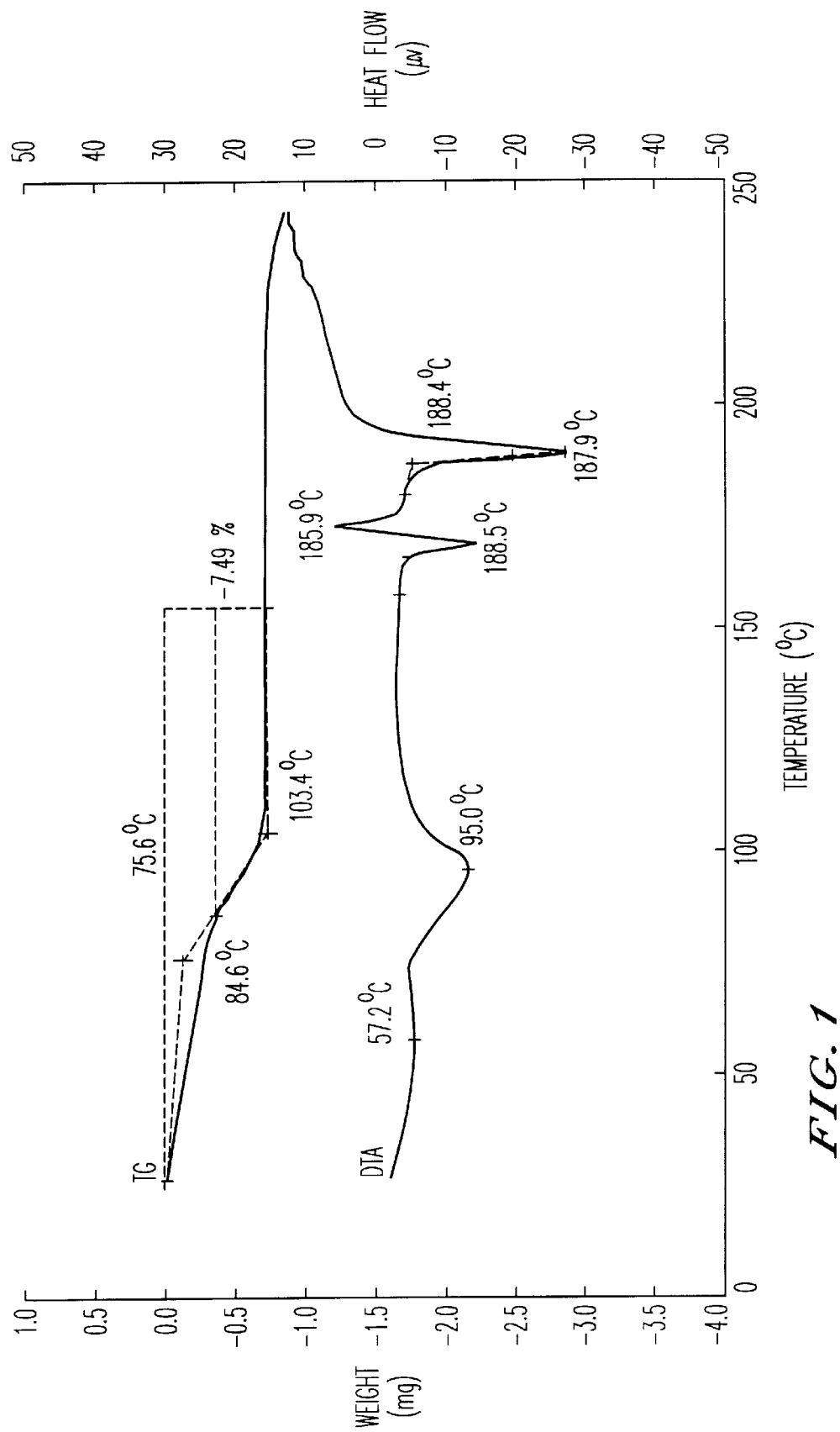
FIG. 1 is a diagram showing the result of thermal analysis of the inventive substance.
Figure 2:
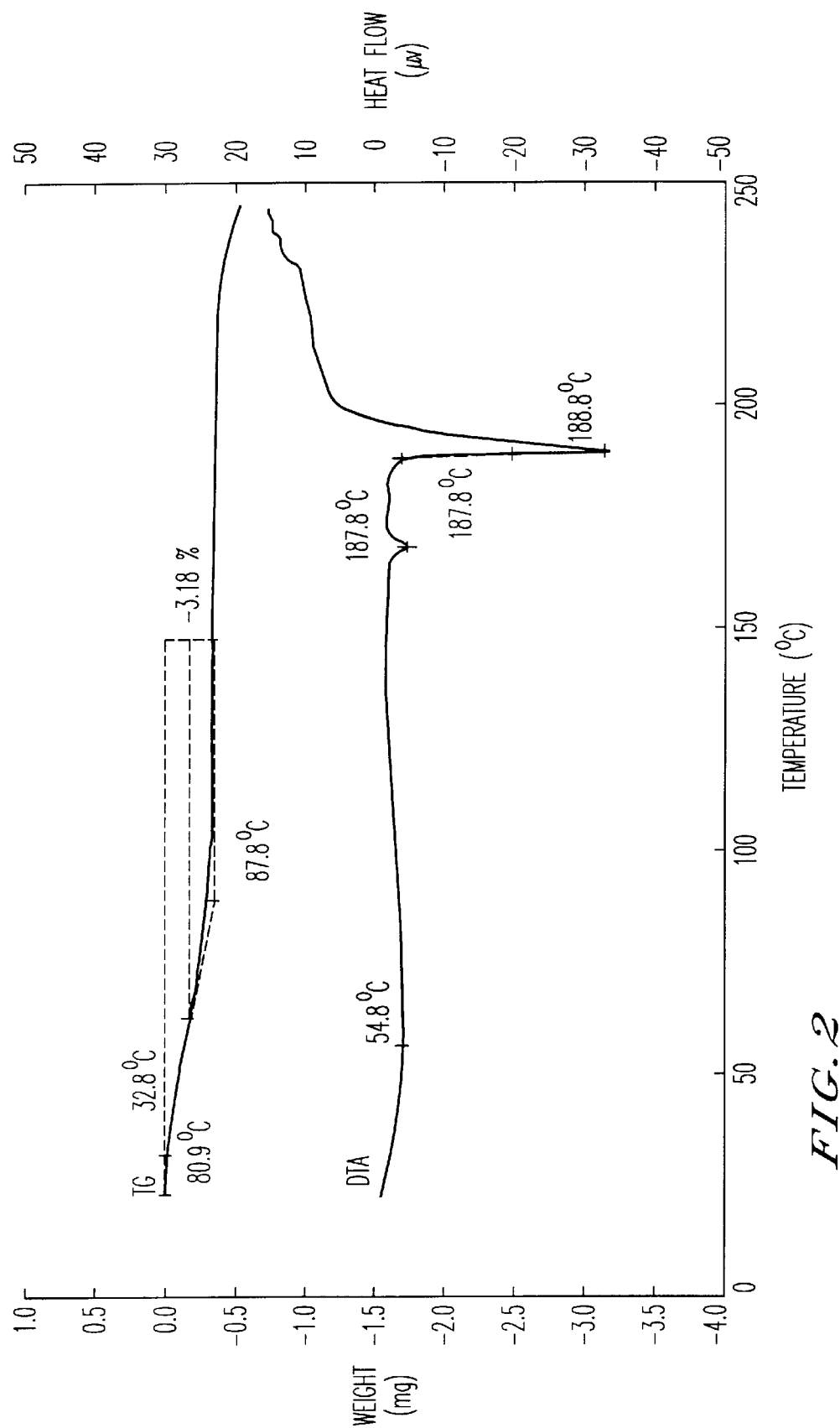
FIG. 2 is a diagram showing the result of thermal analysis of comparative substance.

Employing each about 10 mg of samples of the inventive substance and comparative untreated substance without hot water treatment, heating was performed from room temperature to 240° C. at a temperature-raising velocity of 5° C./min, using α-alumina as a reference, and the gravimetric behavior and the thermal behavior at that time were measured, respectively. The results are shown in FIG. 1 for the inventive substance and in FIG. 2 for the comparative substance.

2) Infrared absorption spectrometry

Figure 3:
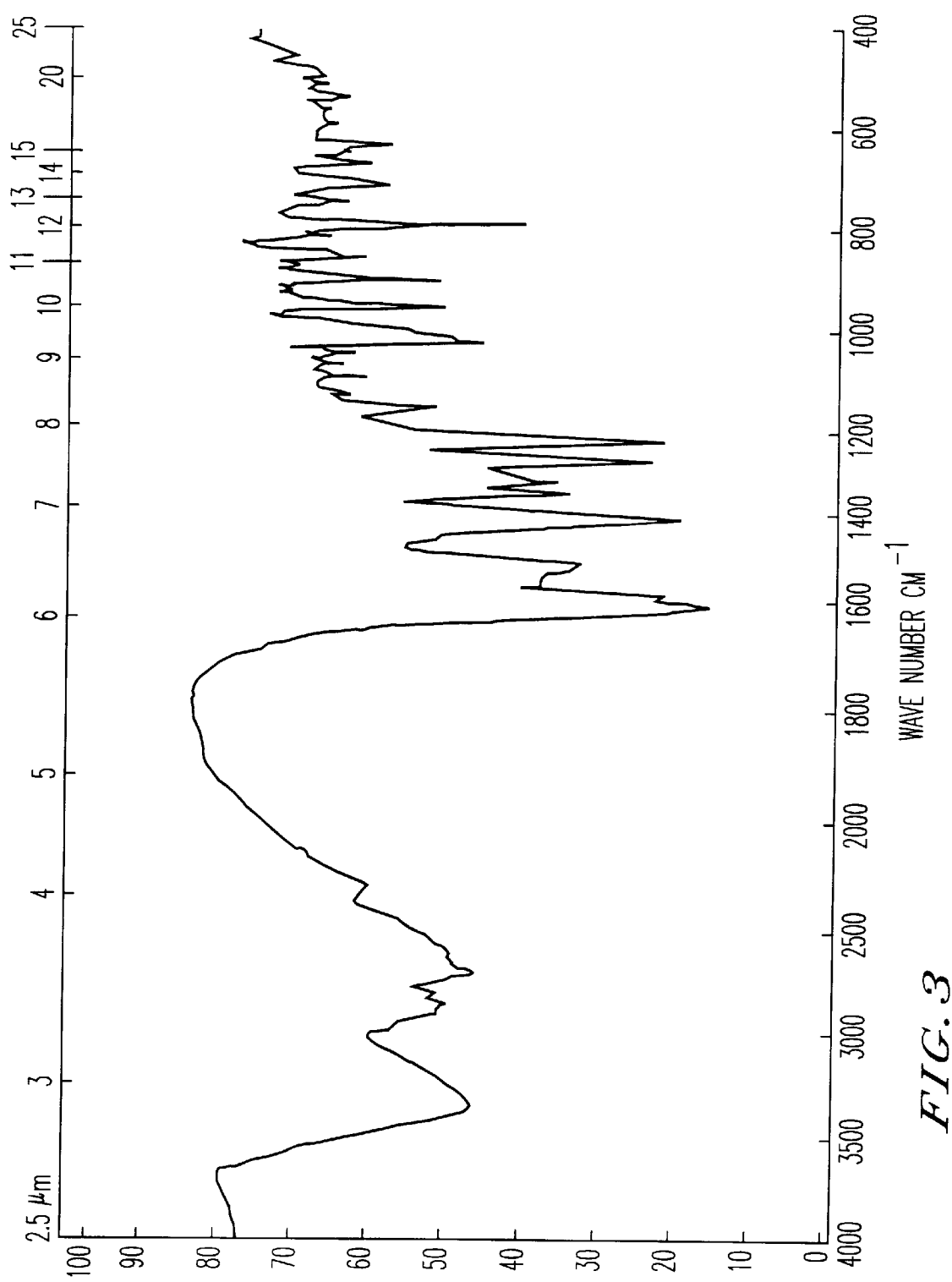
FIG. 3 is a diagram showing infrared spectrum of the inventive substance.
Figure 4:
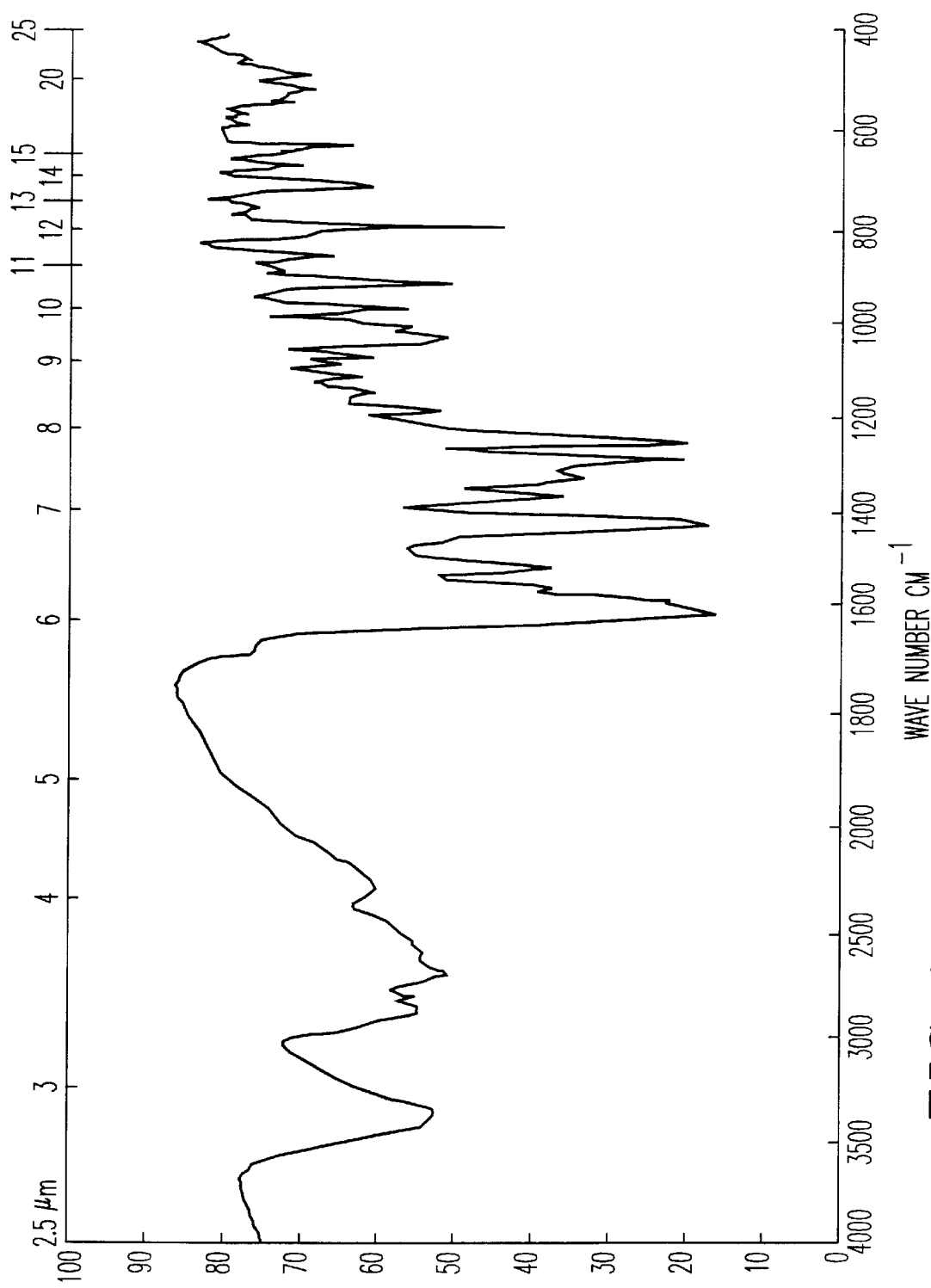
FIG. 4 is a diagram showing infrared spectrum of comparative substance.

Each sample of the inventive substance and untreated substance without hot water treatment was measured by KBr-transmission method. The results are shown in FIG. 3 for the inventive substance and in FIG. 4 for the comparative substance, respectively.

3) Powder X-ray diffraction

Figure 5:
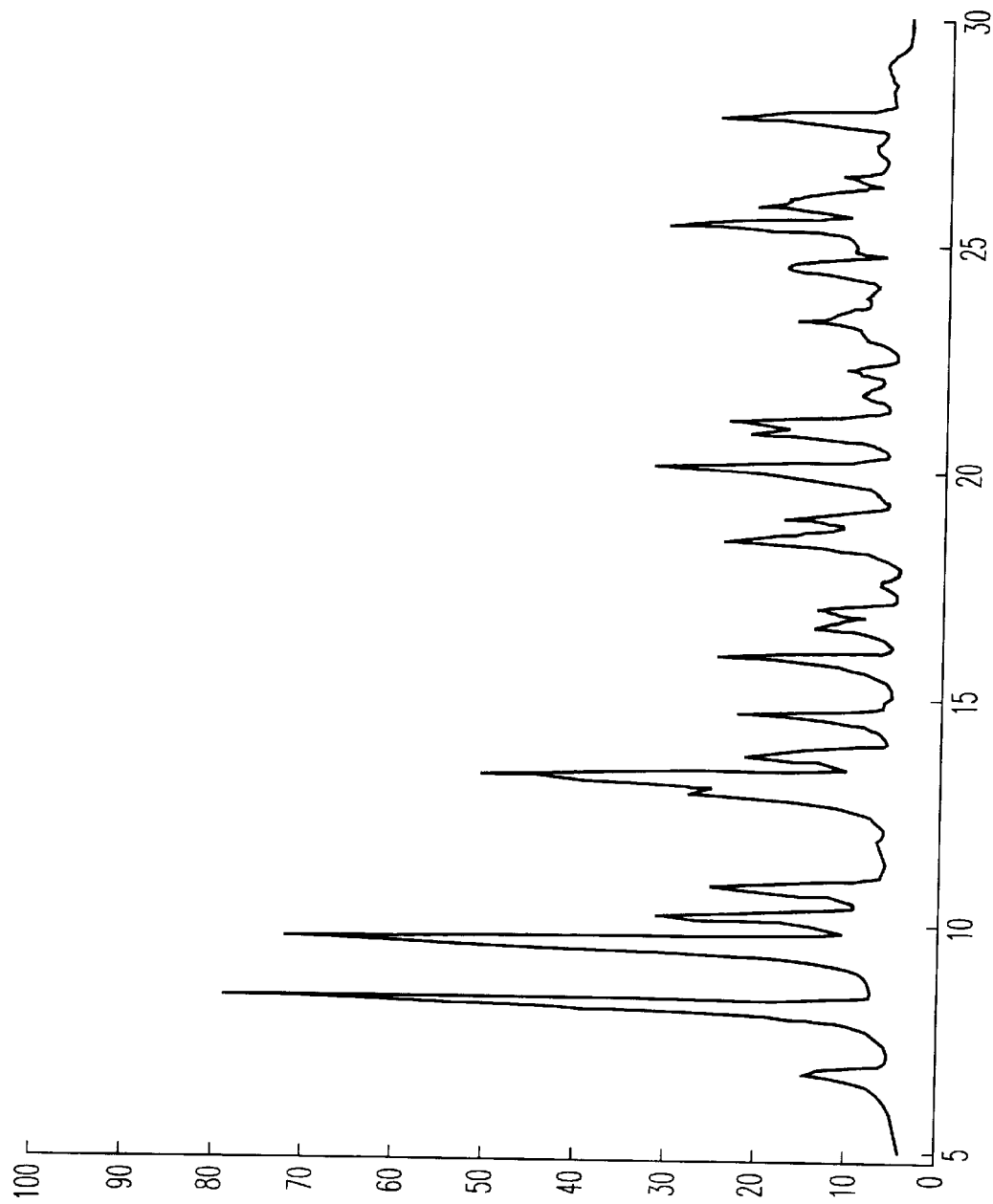
FIG. 5 is a diagram showing the result of X-ray diffraction of the inventive substance.
Figure 6:
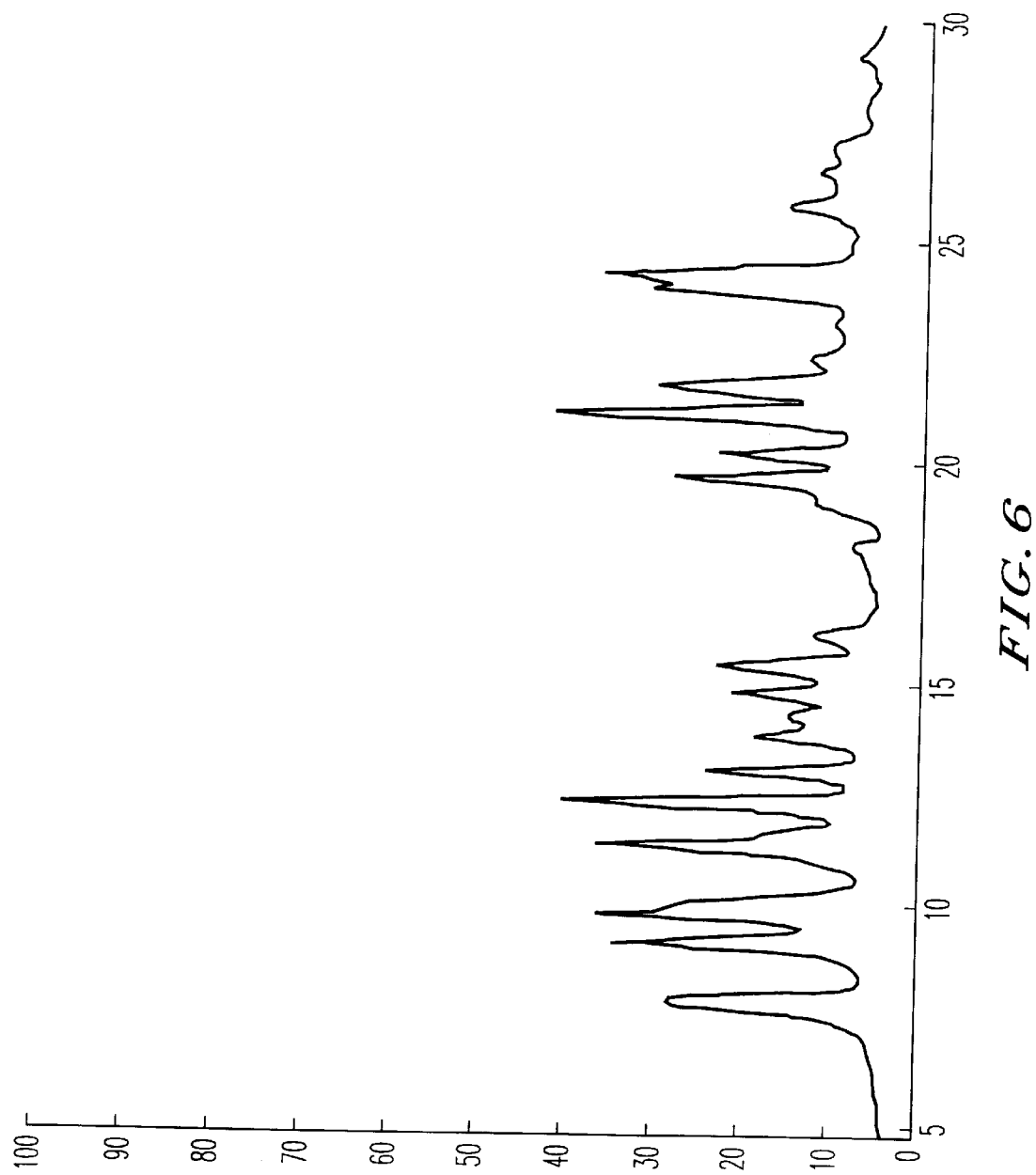
FIG. 6 is a diagram showing the result of X-ray diffraction of comparative substance.

Each sample of the inventive substance and comparative substance was pulverized and measured using a glass sample plate. The results are shown in FIG. 5 for the inventive substance and in FIG. 6 for the comparative substance, respectively.

4) Single crystal X-ray diffraction

Figure 7:
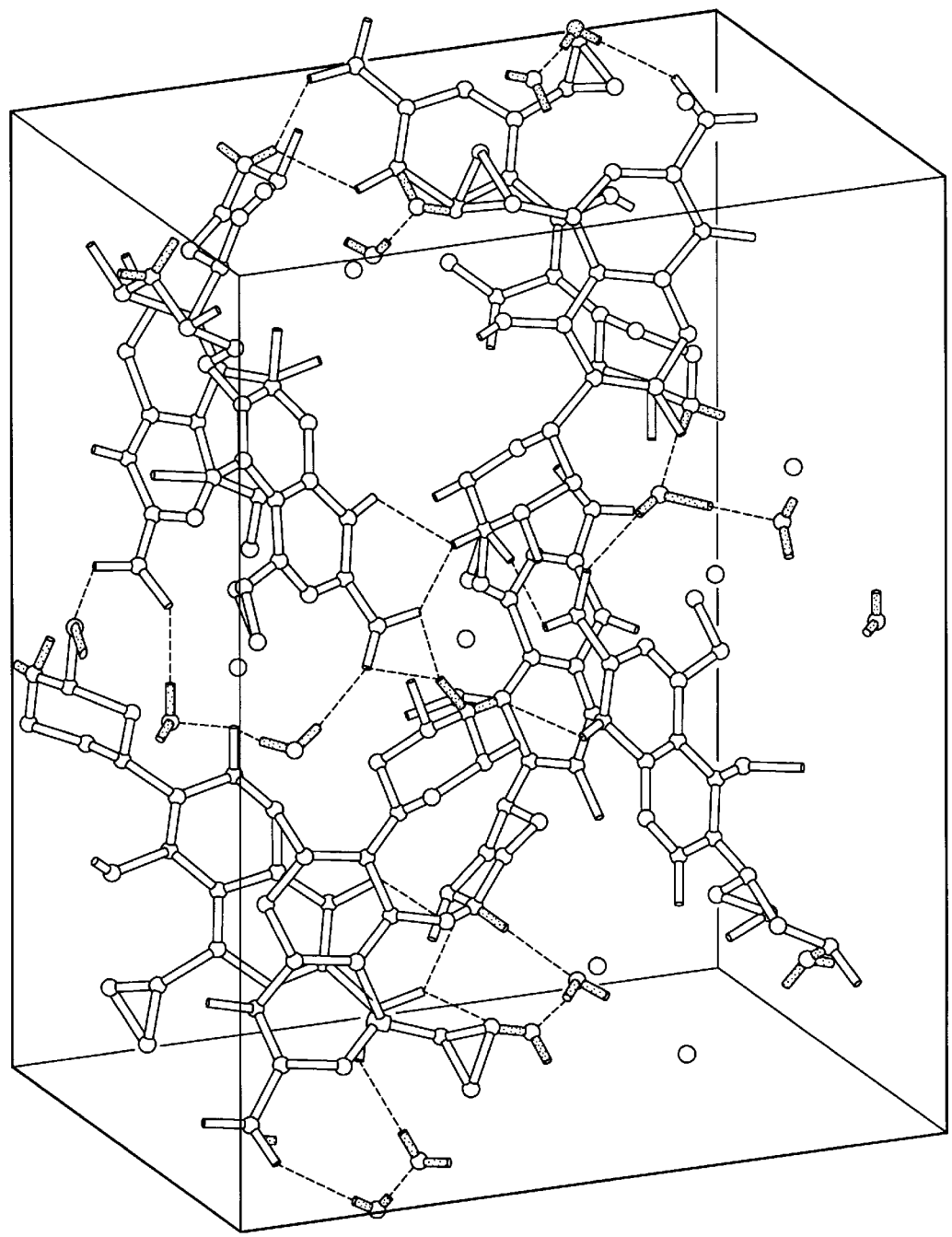
FIG. 7 is an illustrative diagram showing the crystal structure of the inventive substance.

The crystal structure obtained as a result of X-ray diffraction is shown in FIG. 7.

1-Cyclopropyl-6-fluoro-1,4-dihydro-8-methoxy-7-(3-methyl-1-piperazinyl)-4-oxo-3-quinolinecarboxylic acid sesquihydrate retained a constant amount of water under ordinary preservation conditions and was stable.

When comparing the measurement data of thermal analysis (TG/DTA), infrared absorption spectrometry and powder X-ray diffraction between the untreated substance and the inventive hot water-treated substance, the patterns differ obviously, hence it has become clear that the hot water-treated substance and the untreated substance have different crystal forms.

In addition, from the result of single crystal X-ray diffraction, it has been proved that 1-cyclopropyl-6-fluoro-1,4-dihydro-8-methoxy-7-(3-methyl-1-piperazinyl)-4-oxo-3-quinolinecarboxylic acid sesquihydrate contains 8 molecules of 1-cyclopropyl-6-fluoro-1,4-dihydro-8-methoxy-7-(3-methyl-1-piperazinyl)-4-oxo-3-quinolinecarboxylic acid and 12 molecules of water in a unit cell.

Utilizability in the Industry

The inventive 1-cyclopropyl-6-fluoro-1,4-dihydro-8-methoxy-7-(3-methyl-1-piperazinyl)-4-oxo-3-quinolinecarboxylic acid sesquihydrate is excellent in the disintegration and dissolution rate and stable, hence it is very useful for pharmaceutical manufacturing.

Scope of the claim:

1. 1-Cyclopropyl-6-fluoro-1,4-dihydro-8-methoxy-7-(3-methyl-1-piperazinyl)-4-oxo-3-quinolinecarboxylic acid sesquihydrate represented by a formula (1)

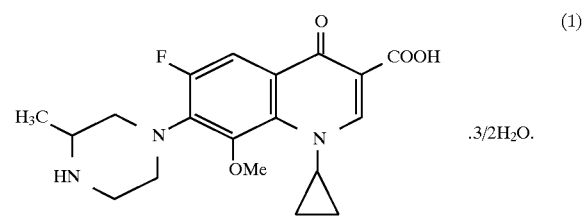

2. A process for producing the compound of claim 1, characterized in that an aqueous suspension of 1-cyclopropyl-6-fluoro-1,4-dihydro-8-methoxy-7-(3-methyl-1-piperazinyl)-4-oxo-3-quinolinecarboxylic acid is treated by heating under stirring.

3. The process of claim 2 wherein said aqueous suspension is heated at a temperature of 50° to 100° C.

4. The process of claim 3 wherein said temperature is 80° to 90° C.

5. The process of claim 2 wherein said aqueous suspension is at a pH in the range 6.0 to 8.0.

6. The process of claim 2 wherein said suspension is hot filtered at the same temperature at which it is treated.

7. The process of claim 6 wherein, after collecting a first crop of crystals, a second crop is obtained by cooling the filtrate to room temperature.

8. The process of claim 3 wherein, after collecting a first crop of crystals, a second crop is obtained by cooling the filtrate to room temperature.

9. The process of claim 2 wherein said aqueous suspension is the suspension obtained after neutralization in the acid-alkali recrystallization during the process of purifying said 1-cyclopropyl-6-fluoro-1,4 dihydro-8-methoxy-7-(3-methyl-1-piperazinyl)-4-oxo-3-quinoline carboxylic acid.

* * * * *